United States Patent [19]

Berke et al.

[11] 4,337,269

[45] Jun. 29, 1982

[54] PRESERVATIVE COMPOSITIONS

[75] Inventors: Philip A. Berke, Madison; William E. Rosen, Summit, both of N.J.

[73] Assignee: Sutton Laboratories, Inc., Chatham, N.J.

[21] Appl. No.: 59,969

[22] Filed: Jul. 23, 1979

[51] Int. Cl.$^3$ ..................... A01N 37/02; A01N 37/12; A01N 55/02

[52] U.S. Cl. .................................. 424/289; 106/210; 252/9; 424/294; 424/311; 424/319; 426/133; 426/320; 426/330.1; 426/330.2; 426/335; 426/532

[58] Field of Search ................ 424/319, 311, 294, 289

[56] References Cited

U.S. PATENT DOCUMENTS 3,002,882  10/1961  van Andel ........................... 424/319
3,068,146  12/1962  Heusser ............................... 424/250
3,291,606  12/1966  Jeffreys .................................. 96/55

FOREIGN PATENT DOCUMENTS 224851  10/1959  Australia .
1492121  5/1969  Fed. Rep. of Germany ...... 424/319
1235690  5/1960  France .
1048507  11/1966  United Kingdom ................ 424/319

OTHER PUBLICATIONS

Krause; C. A. vol. 14, (1920) pp. 56-57.
Martell et al., C. A. vol. 44 (1980) 4420-4421.
Baun; C. A. vol. 34 (1940) 3971.
Rodd "Chemistry of Carbon Compounds", 2nd Ed., vol. ID (1965) p. 167.
H. Krause, Ber., 52, 1211-1222 (1919).
W. Löb, Biochem. Z, 51, 116-127 (1913).

Primary Examiner—Allen J. Robinson
Attorney, Agent, or Firm—Bacon & Thomas

[57] ABSTRACT

A biocidal composition containing the product produced by the reaction of glycine, an alkyl substituted glycinate, or salts of these compounds with formaldehyde is disclosed. The composition effectively inhibits growth of bacteria, yeast and mold in a variety of substances susceptible to microbial contamination.

3 Claims, No Drawings 4,337,269

PRESERVATIVE COMPOSITIONS

BACKGROUND OF THE INVENTION

1. Field of the Invention

The present invention is directed to a composition containing a compound produced by the reaction of glycine, an alkyl substituted glycinate or salts of these compounds with formaldehyde which effectively inhibits microbial growth in a variety of substances.

2. Description of the Prior Art

Reports on the reaction of glycine with formaldehyde is limited to work done over 50 years ago. W. Löb [Biochem. Z., 51, pp. 116–127 (1913)] reported that glycine (also called aminoacetic acid and glycocoll) plus formaldehyde formed the Schiff base in neutral solution and formed methylenediglycine, isolated as the dihydrochloride, in acid solution. Löb did not report isolating a product from reaction in alkaline solution. Following Löb, H. Krause [Ber., 52, pp. 1211–1222 (1919)] described the preparation of sodium or potassium salts of hydroxymethylglycine by low temperature reaction in aqueous solution. Krause also described the preparation of other salts, e.g., barium, lead, silver, copper, mercury and calcium salts, of hydroxymethylglycine from either glycine salt plus formaldehyde or by replacement of the sodium or potassium cation of the hydroxymethylglycine salt.

More recently, N-hydroxymethylglycine is disclosed in U.S. Pat. No. 3,291,606. In that patent, a photographic color image is reported to be protected against fading and discoloration caused by intense tungsten illumination when bathed in an aqueous solution of glycine, glycylglycine or N-hydroxymethylglycine. The source of the N-hydroxymethylglycine is not disclosed.

Recent survey articles discussing the reaction between glycine and formaldehyde have stressed the complexity of the chemistry. See, e.g., Rodd, *The Chemistry of Carbon Compounds*, 2nd Ed. Vol ID (1965) p. 167. For example, while the condensation of the sodium salt of glycine with formaldehyde may be viewed as a simple addition reaction:

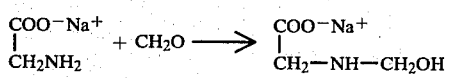

it can also be much more complicated because the hydroxymethyl derivative could dehydrate to a Schiff base, react with another molecule of glycine or polymerize. Thus, rather than term the reaction product simply sodium hydroxymethylaminoacetate, it is more accurate to speak of it as an equilibrium mixture of compounds produced by the reaction of the sodium salt of glycine with formaldehyde. The precise proportions of the particular compounds in the mixture will depend on the particular reaction conditions.

While it is evident that the prior art has long recognized that salts of glycine could be reacted with formaldehyde, there is little disclosure regarding the utility of the reaction product.

SUMMARY OF THE INVENTION

Accordingly, it is a primary object of the invention to utilize the product formed by the reaction of glycine, an alkyl substituted glycinate, or salts of these compounds with formaldehyde in a new and unobvious manner as a biocidal agent which inhibits the growth of microorganisms in substances requiring microbial inhibition.

Another object of the invention is to provide a new and improved biocidal composition containing the reaction product as the primary active ingredient against microbial growth.

Other objects and advantages of the invention will be evident to those of skill in the art upon review of the entire disclosure contained herein.

These objects and advantages are accomplished by providing a biocidal composition consisting essentially of the product produced by the reaction of glycine, an alkyl substituted glycinate, or salts thereof with formaldehyde. By incorporating an effective amount of this composition into a substance requiring microbial inhibition, the substance can be protected against contamination by a variety of microorganisms including bacteria, yeast and mold.

DETAILED DESCRIPTION OF THE INVENTION

The present invention is based upon the discovery that the product produced by the reaction of glycine or a salt of glycine with formaldehyde is a highly effective biocidal agent which inhibits microbial growth in a variety of applications whether they be in solid, liquid or emulsion form. Such applications include, but are not limited to, cosmetics, foodstuffs, pharmaceuticals, paints, cutting oils or fluids, agricultural products, oil drilling fluids, paper industry, embalming solutions, cold sterilization medical and dental equipment, cooling towers, fabric impregnation, latexes, swimming pools, inks, household disinfectants, waxes and polishes, toilet bowl cleaners, bathroom cleaners, laundry detergents, soaps, wood preservatives, hospital and medical antiseptics and adhesives. Obviously, all of these applications involve in vitro use of the product of the invention to inhibit growth of microorganisms.

In addition to the glycine-formaldehyde reaction product, the biocidal composition of the invention may contain other conventional ingredients including other microbial agents, suspending agents, wetting agents, anti-scaling agents, corrosion inhibitors and pH control agents. The resulting biocidal composition is incorporated into the substance for which protection is desired in an amount which is effective for inhibiting microbial growth. Of course the amount of the composition incorporated into the substance as well as the particular additional ingredients will vary depending upon the substance being protected and the environment of use. Generally, substances containing less than 1.0% by weight will be effectively protected from microbial growth in most environments. Principally for economic reasons, concentrations less than about 0.5% are preferred. Those of skill in the art will have little difficulty in selecting specific amounts required for particular uses based upon the information contained herein, especially in the examples.

In preparing the biocidal composition of the invention, a mixture of glycine and a basic reagent, such as an alkali metal hydroxide, is prepared and mixed with formaldehyde. To obtain a salt other than the alkali metal salt, a compound which will cause replacement of the alkali metal cation is added to the reaction mixture. In this manner numerous salts can be prepared including aluminum hydroxymethylaminoacetate, calcium hydroxymethylaminoacetate, magnesium hydroxymethylaminoacetate, copper hydroxymethylaminoacetate and zinc hydroxymethylaminoacetate. When alkyl substituted glycinates are reacted in place of glycine, alkyl hydroxymethylaminoacetates are produced.

After the reaction is complete, an equilibrium mixture of reaction products is obtained as a relatively clear, aqueous solution. The liquid product may be dried to produce a powder, crystalline composition. The powder is the preferred form of the composition of the invention since it is easier to handle than a liquid. When the situation requires a liquid formulation, the powder can be readily dissolved in aqueous media.

The composition of the invention thus provides a highly effective means for preserving substances susceptible to microbial contamination by significantly inhibiting growth of bacteria, yeast and mold. It is readily incorporated into a variety of substances having a variety of forms including liquids, solids and emulsions.

To further illustrate the various aspects of the invention, the following examples are provided. However, it is to be understood that their purpose is entirely illustrative and in no way intended to limit the scope of the invention. In the examples all percentages are given by weight unless otherwise noted.

EXAMPLE 1

Preparation of Sodium Hydroxymethylaminoacetate

A solution of 75 g. (1.00 mole) of glycine in 100 g. (1.00 mole) of 40% aqueous solution hydroxide was treated with 82 g. (1.00 mole) of 37% formaldehyde holding the batch temperature below 50° C. by water cooling. The final solution pH was 11.4. Water was removed slowly at room temperature, and the crystals which formed were collected, washed with cold water, and dried, giving 47 g. (37% yield) of white solid, mp 150°–155° dec. Anal. Found: C, 26.54; H, 4.81; N, 10.86.

EXAMPLE 2

Preparation of Potassium Hydroxymethylaminoacetate

To a solution of 84 g. (1.5 moles) of potassium hydroxide in 127 g. of water was added 112.5 g. (1.5 moles) of glycine. With stirring and cooling, 121.8 g. (1.5 moles) of 37% formaldehyde solution was added slowly at 30°–35° C. The clear colorless solution, pH 11.4, was dried by removal of water, leaving a hygroscopic white powder, mp 162°–184° C. dec. Anal. Found: C, 24.35; H, 3.97; N, 10.13.

EXAMPLE 3

Preparation of Aluminum Hydroxymethylaminoacetate

To a stirred and water-cooled mixture of 90 g. (1.2 moles) of glycine in 96 g. (1.2 moles) of 50% aqueous sodium hydroxide was added 98.4 g. (1.22 moles) of 37% formaldehyde over 30 minutes. The batch temperature was allowed to rise to 60° C. After 20 minutes stirring, the batch was filtered and the clear, colorless solution was allowed to stand at room temperature overnight. A solution of 96.6 g. (0.4 mole) of aluminum chloride hexahydrate in 150 ml. of water was added with stirring, and the precipitate was collected and washed. The product was air-dried overnight to give 172 g. of aluminum hydroxymethylaminoacetate.

EXAMPLE 4

Methyl Hydroxymethylaminoacetate

A solution of 6.3 g. (0.05 mole) methylglycinate hydrochloride in 4.0 g. (0.05 mole) of 50% aqueous sodium hydroxide plus 10 ml. of water was treated with 4.1 g. (0.05 mole) of 37% formaldehyde. The warm solution was stirred at room temperature for 30 minutes to give a solution, pH 6, of methyl hydroxymethylaminoacetate.

EXAMPLE 5

Use as an Antimicrobial Preservative: Challenge Testing a 0.3% Solution of Sodium Hydroxymethylaminoacetate With Various Microorganisms The following procedure for measuring critical killing time was carried out using a gram-positive bacterium (*S. aureus* ATCC 6538), two gram-negative bacteria (*P. aeruginosa* ATCC 15442 and *E. coli* ATCC 10536), a yeast (*C. albicans* ATCC 10231), and a mold (*A. niger* ATCC 9642).

Bacteria

A 24 hour A.O.A.C. broth culture was used for the test. 0.5. ml. of the 24 hour culture was added to 4.5 ml. of the test sample and mixed thoroughly. The sample was then stored at 35° C. in a hot air incubator for the duration of the test. At pre-selected time intervals of 24, 48 and 72 hours, a loopful (0.1 ml.) of the sample was aseptically removed from the incubator and placed in A.O.A.C. broth with Letheen. The tubes containing the inoculated broth were incubated for 48 hours at 35° C. and then examined for microbial growth.

If the sample turned the medium cloudy on the initial subculture, the subculture was incubated for 24 hours at 35° C. and thereafter subcultured again into fresh medium and incubated for 48 hours at 35° C.

Yeast

The same procedure was used as for bacteria, except Sabourand Liquid Medium with Letheen was used in place of A.O.A.C. broth with Letheen.

Molds

The growth of a 7–10 day slant was washed off with 10 ml. of sterile saline. 0.5 ml. of this suspension was added to 4.5 ml. of the sample and mixed thoroughly. The sample was stored at room temperature for the duration of the test. At pre-selected time intervals, a loopful (0.1 ml.) was removed and placed into Sabourand Liquid Media with Letheen and incubated for 7 days at room temperature and then examined for microbial growth.

If the sample turned the medium cloudy on the initial subculture, the subculture was incubated for 24 hours at room temperature. After the 24 hour incubation, the test tube was subcultured again into fresh medium and incubated for 7 days at room temperature.

The results of challenge testing a 0.3% aqueous solution of sodium hydroxymethylaminoacetate were as follows:

| Species | ATCC Number | Subculture After Incubation Times (Days)* | | |
|---|---|---|---|---|
| | | 1 | 2 | 3 |
| P. aeruginosa | 15442 | 0 | 0 | 0 |
| E. coli | 10536 | 0 | 0 | 0 |
| S. aureus | 6538 | 0 | 0 | 0 |
| C. albicans | 10231 | 0 | 0 | 0 |
| A. niger | 9642 | 0 | 0 | 0 |

*Code:
+ = Growth, 0 = No Growth

EXAMPLE 6

Use as a Preservative for Cosmetics

A model shampoo formulation (a water base detergent system) containing the following ingredients:

| Ingredient | % by Weight |
|---|---|
| Triethanolamine lauryl sulfate (40%) | 25.00 |
| Lauryl Diethanolamide | 5.00 |
| Amphoteric-2 | 5.00 |
| Polyoxyethylene Lanolin (50%) | 3.00 |
| Phosphoric Acid | 0.20 |
| Demineralized Water | qs to 100% | was challenge tested without adding preservative and also with added 0.2% sodium hydroxymethylaminoacetate, following the testing procedure described in Example 5. The shampoo was found to be subject to microbial contamination in the absence of preservative, but well-preserved when containing 0.2 sodium hydroxymethylaminoacetate.

| Species | ATCC Number | Subculture After Incubation Time (Days)* | | | |
|---|---|---|---|---|---|
| | | 1 | 2 | 3 | 7 |
| A. Shampoo formulation without added preservative | | | | | |
| P. aeruginosa | 15442 | + | + | + | + |
| E. coli | 10536 | + | + | + | + |
| S. aureus | 6538 | + | + | 0 | 0 |
| C. albicans | 10231 | + | + | + | 0 |
| A. niger | 9642 | + | + | + | + |
| B. Shampoo formulation containing 0.2% sodium hydroxymethylaminoacetate | | | | | |
| P. aeruginosa | 15442 | 0 | 0 | 0 | |
| E. coli | 10536 | 0 | 0 | 0 | |
| S. aureus | 6538 | 0 | 0 | 0 | |
| C. albicans | 10231 | 0 | 0 | 0 | |
| A. niger | 9642 | + | 0 | 0 | |

*Code:
+ = Growth, 0 = No Growth

EXAMPLE 7

Use as a preservative for cosmetics

A commercial cosmetic emulsion which frequently became contaminated with various "house" microorganisms during manufacture was reformulated to contain 0.3% sodium hydroxymethylaminoacetate. Standard challenge testing of 0.3% aqueous solutions of sodium hydroxymethylaminoacetate and of the cosmetic emulsion itself containing 0.3% sodium hydroxymethylaminoacetate with these problem "house" microorganisms showed complete kill within 3 days. In fact, in the cosmetic emulsion itself, the two "house" microorganisms which were the most difficult to kill were killed within 7 days by sodium hydroxymethylaminoacetate at a concentration of only 0.15%.

A. Aqueous solutions of 0.3% sodium hydroxymethylaminoacetate

| Species | Subculture After Incubation Time (Days)* | | |
|---|---|---|---|
| | 1 | 2 | 3 |
| P. aeruginosa #1 | 0 | 0 | 0 |
| P. aeruginosa #2 | 0 | 0 | 0 |
| P. aeruginosa #3 | + | + | 0 |
| Yeast | + | + | 0 |
| Mold | 0 | 0 | 0 |

B. Cosmetic emulsion containing 0.15% sodium hydroxymethylaminoacetate

| Species | Subculture After Incubation Time (Days)* | | | |
|---|---|---|---|---|
| | 1 | 2 | 3 | 7 |
| P. aeruginosa #3 | + | + | + | 0 |
| Yeast | + | 0 | 0 | 0 |

*Code:
+ = Growth, 0 = No Growth

EXAMPLE 8

Use as a preservative for adhesives

A poster paste ashesive based on a potato starch formulation was found to develop odor and mold when stored before use during spring and summer months. Challenge testing of the poster paste slurry with the five microorganisms listed in the *United States Pharmacoepia* XIX, page 588 (1975) for challenging multiple-dose parenteral, otic, nasal and ophthalmic products, showed significant differences between unpreserved poster paste slurry and poster paste slurry containing 0.3% sodium hydroxymethylaminoacetate.

| Species | ATCC Number | Subculture After Incubation Times (Days)* | | | |
|---|---|---|---|---|---|
| | | 1 | 2 | 3 | 7 |
| A. Unpreserved poster paste slurry | | | | | |
| P. aeruginosa | 9027 | + | + | + | + |
| E. coli | 8739 | + | + | + | + |
| S. aureus | 6538 | + | + | + | + |
| C. albicans | 10231 | + | + | + | + |
| A. niger | 16404 | + | + | + | + |
| B. Poster paste slurry containing 0.3% sodium hydroxymethylaminoacetate | | | | | |
| P. aeruginosa | 9027 | 0 | 0 | 0 | |
| E. coli | 8739 | 0 | 0 | 0 | |
| S. aureus | 6538 | 0 | 0 | 0 | |
| C. albicans | 10231 | 0 | 0 | 0 | |
| A. niger | 16404 | 0 | 0 | 0 | |

*Code:
+ = Growth, 0 = No Growth

EXAMPLE 9

Use in lubricating and cutting fluids

A petroleum-based lubricating oil concentrate (15 ml.) was diluted to 500 ml. with tap water and inoculated with a bacterial and mold inoculum which had been maintained in a petroleum base cutting fluid and in a synthetic coolant, respectively. The bacterial inoculum consisted mostly of Fusarium and Cephalosporium species. Microbial counts and re-inoculation was done weekly, and all runs were carried out in duplicate. Experiments were carried out at room temperature (25° C.). In the absence of added preservative, the lubricating fluid was found to contain in excess of $10^5$ organisms/ml. at the first weekly subculture assay after inoculation with bacteria and mold. When the diluted lubricant (coolant emulsion) contained 0.1% sodium hydroxymethylaminoacetate, subcultures after three weekly inoculations and re-inoculations showed less than $10^5$ organisms/ml. Only after the fourth weekly inoculation did the coolant emulsion support microbial growth and show microbial levels in excess of $10^5$ organisms/ml.

EXAMPLE 10

Antimicrobial effectiveness of hydroxymethylaminoacetic acid and its salts; preservation of milk.

The microbial spoilage of whole milk at room temperature was prevented by the incorporation of 0.3% hydroxymethylaminoacetic acid or 0.3% hydroxymethylaminoacetate salt. The following series of tests was terminated after 23 days.

| Preservative added (at 0.3% concentration) to whole milk | Time to spoilage (i.e. development of odor, color, curdling, etc.) |
| --- | --- |
| None | 2 days |
| Hydroxymethylaminoacetic acid | 23 + days |
| Sodium hydroxymethylaminoacetate | 23 + days |
| Potassium hydroxymethylaminoacetate | 23 + days |
| Calcium hydroxymethylaminoacetate | 23 + days |
| Copper hydroxymethylaminoacetate | 23 + days |
| Magnesium hydroxymethylaminoacetate | 23 + days |
| Zinc hydroxymethylaminoacetate | 23 + days |
| Aluminum hydroxymethylaminoacetate | 23 + days |

EXAMPLE 11

Antimicrobial effectiveness of hydroxymethylaminoacetic acid and its salts; preservation of egg The microbial spoilage of whole egg at room temperature was prevented by the incorporation of 0.3% hydroxymethylaminoacetic acid or 0.3% hydroxymethylaminoacetate salt. The following series of tests was terminated after 23 days.

| Preservative added (at 0.3% concentration) to whole egg | Time to Spoilage (i.e. development of odor, and/or color, thickened, separated, etc. |
| --- | --- |
| None | 2 days |
| Hydroxymethylaminoacetic acid | 23 + days |
| Sodium hydroxymethylaminoacetate | 23 + days |
| Potassium hydroxymethylaminoacetate | 23 + days |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for inhibiting microbial growth in a substance requiring microbial inhibition comprising incorporating into the substance in vitro an effective microbial growth inhibiting amount of a condensation reaction product produced by the reaction of glycine, lower alkyl substituted glycinate or salts thereof with formaldehyde in aqueous medium in a molar ratio of about 1:1.

2. The method as defined by claim 1, wherein said reaction product is a member selected from the group consisting of sodium hydroxymethylaminoacetate, potassium hydroxymethylaminoacetate, aluminum hydroxymethylaminoacetate, calcium hydroxymethylaminoacetate, magnesium hydroxymethylaminoacetate, copper hydroxymethylaminoacetate, zinc hydroxymethylaminoacetate, methyl hydroxymethylaminoacetate and hydroxymethylaminoacetic acid.

3. The method as defined by claim 1, wherein said reaction product is incorporated into said substance in an amount less than about 1.0% by weight.

* * * * *